United States Patent [19]

Ness et al.

[11] 4,194,507

[45] * Mar. 25, 1980

[54] DISPOSABLE DIAPER INNER FACING

[75] Inventors: Irving S. Ness, Princeton Borough; Michael R. Fechillas, East Brunswick, both of N.J.

[73] Assignee: Johnson & Johnson, New Brunswick, N.J.

[*] Notice: The portion of the term of this patent subsequent to Apr. 25, 1995, has been disclaimed.

[21] Appl. No.: 842,759

[22] Filed: Oct. 17, 1977

Related U.S. Application Data

[63] Continuation of Ser. No. 663,323, Mar. 31, 1976, Pat. No. 4,085,754.

[51] Int. Cl.² .............................................. A61F 13/16
[52] U.S. Cl. ............................ 128/287; 128/DIG. 30
[58] Field of Search ................................. 128/284, 287

[56] References Cited

U.S. PATENT DOCUMENTS

| | | | |
|---|---|---|---|
| 3,056,406 | 10/1962 | Ness | 128/290 W |
| 3,638,651 | 2/1972 | Torr | 128/284 |
| 3,828,783 | 8/1974 | Kennette et al. | 128/284 |
| 3,848,597 | 11/1974 | Endres | 128/287 |
| 3,885,566 | 5/1975 | Jacob | 128/287 |
| 3,934,588 | 1/1976 | Mesek et al. | 128/284 |
| 3,985,136 | 10/1976 | Cepuritis | 128/284 X |
| 4,085,754 | 4/1978 | Ness et al. | 128/287 |
| 4,085,754 | 4/1978 | Ness et al. | 128/290 W |

Primary Examiner—Robert W. Michell
Assistant Examiner—Milford Juten

[57] ABSTRACT

An improved inner facing for use with disposable diapers containing adhesive tape tabs. The improved inner facing includes a porous nonwoven fabric having at least one entire surface treated with an adhesive release agent so that the treated surface may be a releasable surface for the adhesive tape tabs. The treated fabric is pervious to fluid.

6 Claims, 5 Drawing Figures

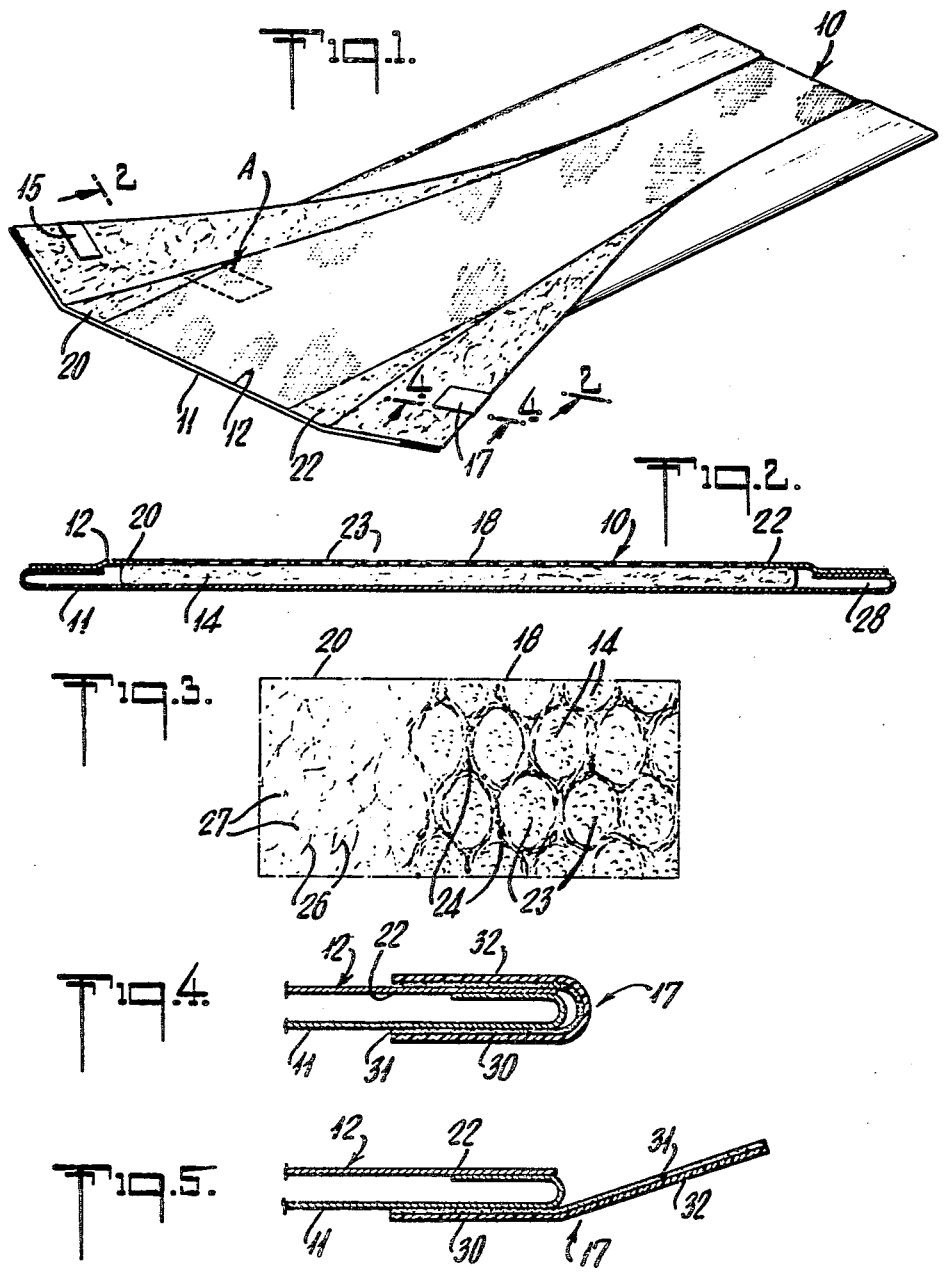

DISPOSABLE DIAPER INNER FACING

This application is a continuation of Application Ser. No. 663,323 filed Mar. 31, 1976, now U.S. Pat. No. 4,085,754.

BACKGROUND OF THE INVENTION

This invention relates to improvements in disposable diapers which utilize adhesive tape tabs for closure purposes. More particularly, this invention pertains to the inner facing of a disposable diaper which acts as a releasable protective surface for the adhesive tape tabs before use.

Disposable diapers with adhesive tape tabs for fastening purposes as well known and have been favorably accepted due to their beneficial features. The advantages of adhesively-treated tape tabs as replacements for pins are easily perceived, and have been put to good use on the known diapers. Though disposable diapers have been improved with the introduction of adhesive tape tab fasteners, a number of problems exist in those tape tab diapers which leave room for further improvement.

A number of the prior art diapers contain adhesive tape tabs which carry individual, removable release or cover sheets. These sheets protect the adhesive surface on the tape tabs during manufacture, storage and before use on the diaper. When the diaper is ready for use the release sheets are completely removed from the tape tab and from the diaper to expose the layer of adhesive beneath. The discardal of the small sheets of release paper poses the problem. Because the person preparing the diaper application, usually around an active infant, has that piece of release sheet in hand, it often becomes awkward to rid oneself of the release paper, hold the infant in position and fasten the tape properly and securely. Also, once the release sheet is discarded it must be done so properly so that the infant does not reach it and place it in his or her mouth, creating further problems.

Other prior art tape tab diapers do not have the discardal problem as above because these diapers contain a protective release sheet which remains fastened to the diaper. To expose the adhesive surface the tape tab is peeled from the release sheet, one surface of which is permanently attached to the diaper. Thus, no discardal of the release paper is required, thereby eliminating those problems associated therewith. However, since the release sheet stays permanently attached to the diaper, usually on the inside surface thereof, it may be an irritant to the wearer of the diaper if the diaper is not applied properly or if the diaper does not fit neatly. Besides this functional problem there are also economic problems inherent in these latter diapers. It adds more expense to not only include a protective paper over the adhesive tape tabs but to permanently fasten one surface of the protective paper to the diaper. The equipment for producing this arrangement to assure proper alignment and registration is also a factor in the economic evaluation of these diapers, especially when considering the high volume manufacture of these products.

Recent attempts have been made to overcome some of the problems associated with releasable protective sheets. In U.S. Pat. No. 3,885,566 there is disclosed an improved disposable diaper in which a water permeable facing sheet comprises areas of water-sensitive or water-soluble adhesive areas underlying the adhesive tape strips such that the adhesive portions of the strips rest releasably against the adhesively treated areas. By this technique no protective release sheets are required because the adhesive sections of the tape strips rest against the releasable sections of the facing material in storage and before use.

Concededly, the technique in U.S. Pat. No. 3,885,566 of eliminating the protective release sheets is one way of accomplishing such a result. However, the narrow scope of this technique, namely providing only water-sensitive or water-soluble adhesive areas, on the facing material, leaves room for use of adhesive agents which are not water-sensitive or water-soluble. Many known and standardly used release agents are water-insoluble and water-insensitive. In this respect, though, it is recognized that there have been attempts prior to the above-mentioned patent to treat portions of disposable diapers with water-insoluble release agents.

In U.S. Pat. No. 3,638,651 a disposable diaper is disclosed having water-insoluble release agents located on portions of the diaper inner facing to protect adhesive sections during storage in cartons and when folded. It is significant to note in the many different embodiments of this patent that the areas or portions of the diaper which contain the release agent are the corners or ends of the diaper. In no instance is it taught or suggested that the release agent be deposited in the portion of the diaper inner facing which covers the delicate body areas of the wearer and which of necessity, must be the most fluid pervious.

One explicable reason why only the ends or corners of this prior art patent are treated, and not the middle highly pervious section of the facing material, lies in the disadvantageous properties associated with the known release agents taught by the reference. While providing release properties to the associated sections of the facing upon which the adhesive tape tabs rest, these water-insoluble agents are known to act as water or fluid repellents while imparting stiffness and boardiness to the coated material. These latter characteristics are the antithesis of the desirable features expected of a disposable diaper; a water-repellent facing material will not allow the secreted fluid to penetrate through the facing material into the highly absorbent inner filling of the diaper; and a stiff, boardy surface in contact with the skin of the wearer readily causes irritation, discomfort and displeasure.

Although it appears logical and practical to treat the facing sheet only in the areas against which the adhesive tape tab will rest, as taught in the two abovementioned patents, this selective treating raises havoc with volumetric production causing economic deficiencies. Alignment and registration of the release areas coordinated with the tabs must be done precisely with the accompanying costs inherent in achieving such precision; furthermore, selective applicators for the release agent, and curing and drying equipment must be provided in line during the diaper production process, all detracting from the economic advantages to be expected from the final product.

SUMMARY OF THE INVENTION

It has now been discovered that disposable diapers using adhesive tape tabs can be made economically and practically with no protective release sheets while overcoming the problems associated with the prior art's attempt to achieve such a product. This new invention primarily eliminates the need for protective release sheets used in conjunction with adhesive tape tabs, whether such release sheets be removable or permanently affixed to the diaper. This elimination of release sheets provides economic savings in the production of disposable diapers, while also solving the discardal problem of release sheets which is both an environmental and a practical compensation.

Another advantage achieved by this new invention lies in the elimination of selective registration of adhesive and release areas under the adhesive tapes or sections of the diaper. Selective registration of adhesive release areas is a cost factor which adds to the expense of the final product, especially in the high volume rates of production expected of disposable diapers. By incorporating an inner facing material having a completely release-agent treated surface in this new invention there is no need for costly selective registration and associated equipment. While release-agent treating the entire surface of the inner facing material produces economic advantages, the new inner facing of the diaper is highly pervious to fluids thereby also providing functionally benefits to this new invention.

Along this line and as a further advantage the design and structure of the preferred embodiment of the new diaper inner facing allows for greater efficiency of the absorbent core of the diaper which in turn provides a drier surface against the delicate portions of the wearer's body. Furthermore, the inner facing remains soft and flexible to provide comfort to the wearer.

In accordance with this new invention a new inner facing for use with disposable diapers containing adhesive tape tabs has been developed. The new inner facing is a porous nonwoven fabric having at least one entire surface treated with an adhesive release agent. Due to that treatment, the treated surface is capable of being a releasable surface for the adhesive tape tabs. The treated fabric remains pervious to fluids. To assure fluid perviousness and an equal distribution of fluid passing through the inner facing it is desirable to have a multiplicity of openings in the fabric substatially uniformly arranged and sufficiently large to allow fluid to pass through after said fabric has been treated with the adhesive release agent.

In the preferred embodiment of the invention which makes the most efficient use of the absorbent core inside the diaper the new inner facing is a nonwoven fabric having a fluid pervious center portion and fluid impervious outer edge portions. Fibers of both fluid pervious and impervious portions extend substantially in the plane of the fabric from one portion to the other so that the portions are integral and connected to each other. Defining the fluid pervious center portion are fibers rearranged to form a multiplicity of openings and groups of fiber segments between the openings. Defining the fluid impervious outer edge portions are fibers flatly assembled in overlapping crossing relation with one another forming irregular, randomly arranged interstices between the fibers. In the fabric of the inner facing the interstices of the outer portions are smaller than the openings in the center portion. At least the outer edge portions are treated with a fluid repellent to render the edge portions fluid impervious, whereas at least one entire surface of the fabric of the inner facing is treated with an adhesive release agent. When the inner facing is used fluid is capable of passing through only the pervious center portion while any portion of the treated surface is capable of being a releasable surface for the adhesive tape tabs.

To employ its most advantageous features the new, improved inner facing is used in a disposable diaper having a fluid impervious outer facing, a fluid pervious inner facing, an absorbent core between the facings and adhesive tape tabs for fastening the diaper around the wearer. The inner facing of the present invention acts as a release surface against which a portion of the adhesive tape tabs lies before the diaper is ready for use. By resting against the releasable surface of the inner facing there is no need to include additional adhesive release sheets with the adhesive tape tabs as is known in the art.

One further aspect of the inner facing of the preferred embodiment of this invention is the treatment of the entire fabric of the inner facing with one agent. This agent contains both fluid repellency and adhesive releasability properties and imparts those properties to the fabric being treated; however, due to the openings in the center portion of the fabric, that portion, while being treated, remains fluid pervious.

BRIEF DESCRIPTION OF THE DRAWINGS

These and other advantages, features and aspects of the invention will become apparent upon reading the following detailed description and upon reference to the accompanying drawings wherein:

FIG. 1 is a perspective view of the preferred disposable diaper including the new, improved inner facing;

FIG. 2 is a cross-sectional view taken along lines 2—2 of FIG. 1;

FIG. 3 is an enlarged fragmentary plan view of area A of FIG. 1 depicting the fluid pervious center portion and one of the outer fluid impervious portions of the inner facing;

FIG. 4 is a cross-sectional view taken along lines 4—4 of FIG. 1;

FIG. 5 is a cross-sectional view of the adhesive tape tab in a ready position for fastening the diaper around the wearer.

While the invention will be described in connection with a preferred embodiment, it will be understood that it is not intended to limit the invention to that embodiment. On the contrary, it is intended to cover all alternatives, modifications and equivalents as may be included within the spirit and scope of the described invention.

DETAILED DESCRIPTION OF THE INVENTION

Turning to the drawings wherein the preferred embodiment is illustrated, a disposable diaper 10 is shown. Diaper 10 is composed of a fluid impervious outer facing 11, such as a thin film, flexible plastic material, a fluid pervious inner facing 12, an absorbent core 14, such as a layer of fluffed woodpulp, layers of creped cellulose, and the like, and adhesive tape tabs 15 and 17 for fastening the diaper around the wearer. While this combination of diaper components, in general, is well known, the advantages mentioned above are achieved by the inclusion of the improved inner facing 12, about which this invention is most directly concerned.

As seen more clearly in FIGS. 1-3 the inner facing 12 is shown in its position on the disposable diaper 10. It is the purpose of the inner facing 12 to provide a surface which contacts the skin of the wearer while acting as a medium to convey body fluids to the absorbent core 14 in the internal portion of the diaper. As the inner facing 12 touches the wearer's skin it is very desirable to provide such a facing which will remain as dry as possible during use while remaining soft and comfortable so as to eliminate irritation. The inner facing 12 shown is a nonwoven fabric which is soft, smooth, and stable and contains fibers disposed in two distinctly different arrangements. In the center portion 18 of the inner facing 12 the fibers are arranged so as to provide a fluid pervious portion; in the outer edge portions 20 and 22 the fibers are so arranged so as to provide portions which are fluid impervious. The center portion 18 and outer edge portions 20 and 22 are integral in nature with each other, i.e., the fabric is one continuous sheet or structure comprised of portions having different fiber arrangements. Portions 18, 20 and 22 are connected by fibers extending substantially in the plane of the fabric from one of said portions to the other; the fibers are joined together by fibers which enter into the structure of and are integral with both of the different portions.

In the center portion 18 of the inner facing the fibers are arranged to form a multiplicity of openings 23 preferably substantially uniformly arranged, and groups 24 of fiber segments between the openings. Preferably, the openings 23 are substantially uniformly regular and arranged in a predetermined pattern. The configuration of the openings 23 may be varied into whatever geometrical shape is desired or which is practicably attainable. As a result of the openings 23, this portion of the facing is very fluid pervious and readily allows fluid to pass through into the absorbent core 14 which is positioned directly beneath the center portion 18 of the facing. The uniform disposition of the openings 23 also distributes the passing fluid more evenly and consistently into the absorbent core 14. In order to assure the fluid pervious characteristic of this center portion, especially in view of the subsequent fluid repellent and adhesive release treatments, as hereinafter described, it has been found that the openings 23 should be defined according to that end. For instance, in the inner facing fabric being described the openings 23 must be large enough to let fluid pass through the fabric after it has been fluid repellent and adhesive release treated, but must not be so large that fibers from the absorbent fluff or pulp core 14 beneath the inner facing may be readily pulled through those openings 23. Also in this respect the larger the opening the more rough the fabric since the fibers become bunched closer together between holes thereby tending to raise those fiber areas. It has been found that individual openings 23 having an area between 0.00126 and 0.0276 square inches (0.00813 and 0.178 sq. cm.) in the inner facing provide the requirements explained above. In those instances where the absorbent core 14 of fluff or pulp has been wrapped with tissue or the like the maximum hole size may be increased to any practicable size since the tissue-wrap eliminates the problem of fiber pullout.

To provide for uniform disposition of the passing fluid through the inner facing in accordance with the opening size requirements, inner fabrics having between 29 and 250 openings per square inch (about 5 and 39 openings per sq. cm.) give the most satisfactory results of this invention.

Bordering and separating the openings 23 are groups 24 of fiber segments. These groups 24 are preferably in substantial parallelism with corresponding portions of the perimeters of the holes and provide a substantially continuous fibrous border for each opening 23. As a result of the parallelism and compacted nature of the fiber segments of the groups 24 the cross-section of the groups is often yarn-like in appearance. When fluid strikes the center portion 18 of the inner facing, the capillary effect of the parallel fiber segments in the groups 24 also assists in uniformly distributing the fluid into the underlying absorbent core 14. The main purpose of the groups 24, while assisting in the distribution of passing fluid is, however, to distinctly define the openings 23 through which the fluid must pass to be absorbed in the core 14.

Outer edge portions 20 and 22 of the inner facing consist of fibers 26 flatly assembled in overlapping crossing relation with one another forming irregular, randomly arranged interstices 27 between the fibers 26. The interstices 27 are very small, smaller than the openings 23 in the center portion, and are sufficiently closely spaced so that a subsequent fluid repellent treatment renders the outer portions 20 and 22 fluid impervious. Consequently, due to the impervious nature of the outer portions 20 and 22 fluid striking the inner facing will only penetrate through the openings 23 in the fluid pervious center section 18. Furthermore, the impervious nature of the outer edge sections 20 and 22 assists in retaining fluid within the absorbent core 14 thereby increasing the efficiency of the absorbent core.

Specifically, as seen more clearly in FIG. 2, fluid striking the inner facing 12 penetrates through the openings 23 into the absorbent core 14 below. Should any excess fluid flow to the sides of the core 14 the fluid is prevented from flowing out due to the trap 28 provided at the edge of the diaper. The trap 28 is a folded edge of the fluid impervious outer film 11 of the diaper and is sealed, such as by adhesive means, to the outer edge 22 of the inner facing. Since the outer edge 22 of the inner facing is also fluid impervious an effective barrier is created at the edges of the diaper to prevent the fluid from running out. As a result the fluid will tend to be absorbed by the absorbent core which will retain the fluid, although in a saturated condition, thereby making more efficient and effective use of the absorbent core. While the outer edges 20 and 22 of the inner facing assist in creating a fluid pervious barrier, the fibrous content of the outer edges allows those portions to remain soft and comfortable against the delicate body areas of the diaper wearer.

Fibers of which the inner facing fabric may be made include many natural fibers such as cotton, wool, woodpulp and the like, and synthetic fibers such as viscose rayon, nylon, cellulose acetate, and other fibers either above or blended in various combinations.

The fabric comprising the inner facing of this invention may be made in accordance with the teachings of U.S. Pat. No. 3,056,406 and 2,862,251, which patents are specifically incorporated herein by reference. Methods and apparatuses for producing the fabric of the inner facing are explained thoroughly in those patents.

Having provided a fabric with center and edge portions as described above, before that fabric is incorporated in its respective position in the disposable diaper it is subjected to a finishing treatment. Where practical, at least the outer edge portions are treated with a fluid repellent. By such treatment and due to the closely spaced interstices between the fibers in the outer portions, those portions are rendered fluid impervious. Of course, if it is not practical to treat only the outer edge portions of the inner facing fabric, the entire fabric may be treated with a fluid repellant. As a matter of fact the most direct, simple and economical way to fluid repellent treat the fabric is by treating the entire fabric. Since the openings in the central portion of the fabric are much larger than the interstices in the outer edge portions, the fluid repellency treatment does not clog the openings thereby preserving the pervious nature of the center portion. Furthermore, due to the significant amount of open area in the center portion the overall treatment does not detract from the softness of the fabric in that area which is in contact with the skin of the wearer.

Not only is the fabric of the inner facing treated so that the outer edge portions become fluid impervious, but it is also treated with an agent so that the overall fabric has adhesive release characteristics; i.e., treated so that adhesive materials will not adhere to the surface of the fabric of the inner facing. While the treatment of fluid repellency and adhesive releasability may be done in two steps or with two separate agents, it is preferable to treat the entire surface of the fabric or the entire fabric itself with one agent containing both fluid repellency and adhesive releasability properties. In this way the outer edge portions of the inner facing fabric will become fluid repellent while any surface of the inner facing is capable of being a releasable surface for the adhesive tape tabs before the tabs are used for fastening purposes.

Techniques of treating the inner facing fabric with an agent to impart the above described properties include fabric impregnation; saturation; gravure application, e.g., rotogravure; spraying; kiss-coating, etc.

Due to the release agent treatment of the inner facing fabric there is no need to include additional release sheets for the adhesive tape tabs in order to protect the adhesive material on the tabs before the diaper is to be used. For instance, as seen in FIGS. 1, 4 and 5 a portion 30 of an adhesive tape tab 17 is attached to the outside film 11 of the diaper. A layer of pressure-sensitive adhesive material 31 coats one surface of the tape tab 17 providing the means for fastening the portion 30 to the diaper. The remaining adhesive portion 32 is extendable beyond the edge of the diaper as best seen in FIG. 5. When in the packaged or storage condition, before the diaper is ready to be used, the extendable portion 32 of the tab is wrapped around the edge of the diaper in a direction generally back over itself as depicted in FIG. 4. In the preferred embodiment illustrated in the drawings, the inner facing 12 has its outer edges 20 and 22 extend to the outer edge of the diaper itself. Of course, the entire inner facing, including the outer edges, has been treated so as to readily release adhesive materials. These release properties allow the extendable portion 32 of the tape tab to overlie and rest upon or be pressed against the outer edge 22 of the inner facing. By resting upon the releasable outer edge 22 the adhesive material 31 on the extendable portion 32 is protected from accidental sticking or from oxidation in that period before the diaper is ready to be placed on the wearer.

When the diaper is to be used the extendable portion 32 of tape is merely lifted from the releasable surface 22 of the inner facing, and is then in position to perform its fastening function. The release treated inner facing allows the tape tab to be separated from the inner facing with little or no fibers from the facing adhering to the adhesive material. Even if a small amount of stray fibers should adhere to the adhesive material on the tape it is not a significant amount that would diminish the fastening strength of the tape tab that secures the diaper around the wearer.

While the foregoing description and accompanying drawings are related to the preferred inner facing which makes maximum use of the absorbent inner core, rendering the core more efficient, modifications and adaptions of that embodiment may be readily accomplished which are within the purview of this invention. For instance, when maximum efficiency of the absorbent core is neither desired nor necessary, and when it is only the elimination of the protective release sheets which is sought, the inner facing does not have to include the bifurcated limitations of the preferred embodiment. In its broadest sense this latter embodiment of an inner facing merely to eliminate protective release sheets is satisfied by use in a disposable diaper of the type described above of a porous nonwoven fabric having at least one entire surface treated with an adhesive release agent; in some cases it may be more feasible to treat the entire fabric. By such a treatment no selective deposition of release agent is required thereby eliminating the expense and problems associated therewith. This treated surface becomes the surface against which the adhesive tape tabs lie so that the adhesive coatings are protected before use of the diaper. It is necessary, however, to have a nonwoven fabric for an inner facing with sufficient porosity to render the treated fabric fluid pervious after the fabric has been adhesive-released treated. One manner of assuring such porosity is to include a multiplicity of openings through the nonwoven fabric. A fabric with openings substantially uniformly arranged allows for even distribution of the fluid as it passes through the inner facing to the absorbent core.

Any of the well known agents which impart adhesive release properties to a surface may be employed in treating the fabric. Silicone containing agents and compounds are suitably adaptable for use in this invention. Since many of the known adhesive release agents also impart fluid repellency properties to the surface on which they are applied these agents are preferably used in this invention especially when attempting to gain maximum efficiency of the absorbent core in the diaper. In this regard one agent with both adhesive release and fluid repellency properties is applied to the inner facing fabric; at least the center portion of any inner facing used in this invention always remains pervious to fluid even after coated with the agent due to the size of the openings through the fabric. By the presence of these openings the selection of adhesive release agent is broadened to include many classes of materials with release properties, including, but not limited to, those inherently or otherwise having fluid repellency properties. Furthermore, the fact that the structure of the pervious portion of the inner facing allows fluid to pass through after the treatment allows the adhesive agent to be applied on the entire surface of the inner facing rather than being selectively deposited and aligned in small, specifically defined areas.

Classes of adhesive release agents which also have fluid repellent properties for treatment of the inner facing include non-ionic water emulsions of reactive silicones such as ESTRASIZE S-4 (Crown Metro); reactive non-ionic heterocyclic condensates such as SUNSIZE 133 (Sun Chemical); reactive water-soluble Werner-type complexes such as QUILON M (Du Pont); fluoro-carbon type repellents such as SCOTCHBAN (Minnesota Mining and Manufacturing); sterotochromic chloride such as KROMYL-S (Crown Metro); and water-soluble or water-dispersable waxes such as ESTRASIZE N zirconium wax (Crown Metro). These classes of agents may be used individually or in various mixtures or blends. Also, these agents are only representative of the types and varieties of release agents which may be selected in accordance with this invention.

The invention will be further illustrated in greater detail by the following specific examples. It should be understood, however, that although these examples may describe in particular detail some of the more specific features of this invention, they are given primarily for purposes of illustration, and the invention in its broader aspects is not to be construed as limited thereto.

EXAMPLE I

An inner facing for a disposable diaper is produced as shown particularly in FIGS. 1 and 3 of the drawings. The processes and apparatuses as described in U.S. Pat. Nos. 3,056,406 and 2,862,251 are employed to produce the inner facing which is comprised of rayon fibers, generally having a length of 2 inches (5.08 cm.) and having a 1.5 denier, the fabric weighing about 250 grains/sq. yd. (19.4 g./sq.in.). The inner facing contains a fluid pervious center portion and fluid impervious edge portions, the fibers of the edge and center portions being interconnected to form an integral fabric. In the center portion there are 95 openings per square inch (approx. 15 openings/sq. cm.), substantially uniformly distributed, each opening having an area of 0.00385 square inches (0.0248 sq. cm.). One entire surface of this inner facing is sprayed with SUNSIZE 133 release agent-fluid repellent so that the entire surface is rendered adhesively releasable, and the edge portions are also rendered fluid repellent while the center portion remains fluid pervious due to the openings therein. This treated inner facing is included in a disposable diaper also comprised of a fluid impervious outer facing, an absorbent core between facings and adhesive tape tabs for fastening purposes. The outer edges of the inner facing extend to the outer edges of the diaper itself, so that the fastening portions of the adhesive tape tabs rest against the treated surface of the outer edges of the inner facing while in storage and before diaper use. No additional protective release sheets are required for the adhesive tape tabs, and, in use, the diaper effeciently contains fluid within the absorbent core particularly due to the specific construction of the new inner facing.

EXAMPLE II

An inner facing is produced and is incorporated in a disposable diaper as in Example I, except that in the center portion there are 225 openings per square inch (approx. 35 openings/sq. cm.), each opening having an area of 0.00159 square inches (0.0103 sq. cm.). One entire surface of this inner facing is gravure-treated with SCOTCHBAN FC813 release agent-fluid repellent so that that entire surface is rendered adhesively releasable, and the edge portions are also rendered fluid repellent while the center portion remains fluid pervious due to the openings therein. When this inner facing is used in the disposable diaper no additional protective release sheets are required for the adhesive tape tabs, and, in use, the diaper efficiently contains fluid within the absorbent core particularly due to the specific construction of the new inner facing.

EXAMPLE III

An inner facing for a disposable diaper is produced according to the processes and apparatuses described in U.S. Pat. No. 2,862,251. The inner facing is comprised of polyvinylalcohol fibers, generally having a length of 1.73 inches (4.4 cm.) and having a 1.4 denier, the fabric weighing about 240 grains per square yard (18.6 g./sq. in.). Distributed substantially uniformly throughout the entire inner facing are openings numbering 49 openings per square inch (approx. 8 openings/sq. cm.), each opening having an area of 0.00785 square inches (0.0506 sq. cm.). One entire surface of this inner facing is saturation treated with a 50:50 blend of ESTRASIZE S-4 and KROMYL-S release agent-fluid repellent so that that entire surface is rendered adhesively releasable, but the fabric remains fluid pervious due to the openings therein. This treated inner facing is included in a disposable diaper also comprised of a fluid impervious outer facing, an absorbent core between facings and adhesive tape tabs for fastening purposes. The diaper is constructed and folded so that, while in storage and before use, the fastening portions of the adhesive tape tabs rest against the treated surface of the inner facing. No additional protective release sheets are required for the adhesive tape tabs, and, in use, fluid readily passes through the openings in the inner facing into the absorbent core.

Thus, it is apparent that there has been provided, in accordance with the invention, an improved inner facing for use with disposable diapers that fully satisfies the aims, advantages and aspects set forth above. While the invention has been described in conjunction with specific embodiments thereof, it is evident that many alternatives, modifications and variations will be apparent to those skilled in the art in view of the foregoing description. Accordingly, the plenary invention is intended to embrace all such alternatives, modifications and variations as fall within the spirit and broad scope of the described invention.

What is claimed is:

1. In a disposable diaper of the type having a fluid impervious outer facing, a fluid pervious inner facing, an absorbent core between said facings and adhesive tabs for fastening the diaper around the wearer thereof, an improved inner facing comprising a porous nonwoven fabric having at least one entire surface thereof being treated with a water insoluble adhesive release agent whereby that surface is capable of being a releasable surface for said adhesive tape tabs, said porous nonwoven fabric having a multiplicity of openings therethrough, which are sufficiently large to allow fluid to pass through after said fabric has been treated with a water insoluble adhesive release agent, causing said treated fabric to be pervious to fluid.

2. A disposable diaper as defined in claim 1 wherein said entire nonwoven fabric is treated with a water insoluble adhesive release agent.

3. A disposable diaper as defined in claim 1 wherein said inner facing is the releasable surface against which an adhesive portion of each of said adhesive tape tabs lies before said diaper is ready to be used.

4. In a disposable diaper of the type having a fluid impervious outer facing, a fluid pervious inner facing, an absorbent core between said facings and adhesive tabs for fastening the diaper around the wearer thereof, and improved inner facing comprising a nonwoven fabric having a fluid pervious center portion and fluid impervious outer edge portions, at least one entire surface of said fabric being treated with a water insoluble adhesive release agent whereby when said inner facing is used fluid is capable of passing through only the pervious center portion of the fabric and any portion of said treated surface is capable of being a releasable surface for said adhesive tape tabs, and wherein said fluid pervious and said fluid impervious portions are integral and are connected by fibers extending substantially in the plane of the fabric from one of said portions to the other, said fluid pervious center portion being defined by fibers rearranged to form a multiplicity of openings and groups of fiber segments between said openings, said fluid impervious outer edge portions being defined by fibers flatly assembled in overlapping crossing relation with one another forming irregular, randomly arranged interstices between said fibers, said interstices being smaller than said openings, said outer edges being treated with a fluid repellent to render said edge portions fluid impervious.

5. A disposable diaper as defined in claim 4 wherein the entire fabric is treated with a fluid repellent with said outer edge portions being rendered fluid impervious but said center portion remaining fluid pervious due to said openings located therein.

6. A disposable diaper as defined in claim 5 wherein said fluid repellent and a water insoluble adhesive release agent are one agent containing both fluid repellency and adhesive releasability properties.

* * * * *